United States Patent
Liu et al.

(10) Patent No.: US 6,722,361 B2
(45) Date of Patent: Apr. 20, 2004

(54) POSITIONING AND BIT-PROOF THROAT MASK RETAINER

(75) Inventors: Ching-San Liu, Taipei-Chung (TW); Kung-Chi Wang, Chang-Hua Hsien (TW)

(73) Assignee: All-scope Co., Ltd., Feng-Yuan (TW)

( * ) Notice: Subject to any disclaimer, the term of this patent is extended or adjusted under 35 U.S.C. 154(b) by 0 days.

(21) Appl. No.: 10/118,515

(22) Filed: Apr. 9, 2002

(65) Prior Publication Data

US 2003/0188742 A1 Oct. 9, 2003

(51) Int. Cl.[7] ............................ A61M 16/00; A61M 5/32
(52) U.S. Cl. ............................ 128/200.26; 128/207.14; 604/174
(58) Field of Search ................ 128/200.24, 200.26, 128/206.29, 207.14, 207.15, 846, 848, DIG. 26, 859–862; 606/108, 196; 623/9; 604/77, 174

(56) References Cited

U.S. PATENT DOCUMENTS

| | | | | |
|---|---|---|---|---|
| 4,198,970 A | * | 4/1980 | Luomanen | 128/207.15 |
| 4,351,331 A | * | 9/1982 | Gereg | 128/207.17 |
| 4,425,911 A | * | 1/1984 | Luomanen et al. | 128/200.26 |
| 4,640,273 A | * | 2/1987 | Greene et al. | 128/861 |
| 5,024,218 A | * | 6/1991 | Ovassapian et al. | 128/200.26 |
| 5,069,206 A | * | 12/1991 | Crosbie | 128/207.17 |
| 5,174,284 A | * | 12/1992 | Jackson | 128/200.26 |
| 5,533,523 A | * | 7/1996 | Bass et al. | 128/859 |
| 5,590,643 A | * | 1/1997 | Flam | 128/200.26 |
| 5,655,528 A | * | 8/1997 | Pagan | 128/207.14 |
| 5,746,202 A | * | 5/1998 | Pagan | 128/207.14 |
| 6,257,238 B1 | * | 7/2001 | Meah | 128/859 |
| 6,318,371 B1 | * | 11/2001 | Tyszkiewicz | 128/859 |
| 6,533,761 B2 | * | 3/2003 | Bertoch et al. | 604/174 |

\* cited by examiner

Primary Examiner—Aaron J. Lewis
Assistant Examiner—Teena Mitchell

(57) ABSTRACT

A positioning and bit-proof throat mask retainer is a flexibly and slightly hard tube capable of being adhered to an upper side of a throat mask respiratory siphon. A lower side of the retainer is matched with an arc shape of the respiratory siphon and has a hollow cambered structure and an upper side of the retainer is suitable for the upper side of the oral cavity. A front end of the retainer is bent upwards to be formed as a resisting portion for resisting against an upper jaw of the patient along the cambered shape of the upper jaw. By the supporting of the upper jaw, the retainer is fixed to the mouth of a patient, thereby, having a function of guiding and positioning the respiratory siphon.

1 Claim, 4 Drawing Sheets

FIG. 4-A

POSITIONING AND BIT-PROOF THROAT MASK RETAINER

BACKGROUND OF THE INVENTION

1. Field of the Invention

The present invention relates to retainers, and particularly to a positioning and bit-proof throat mask retainer, wherein when the patient contracts in surgery, the retainer is exactly positioned in the mouth of the patient. As the teeth of patient bit together, since the retainer is hard and flexible, it can resist against the upper and lower teeth of the patient. Thereby, the patient will not be hurt.

2. Description of Related Art

The throat mask discussed in the present invention is a tool for assisting the patient to breath in surgery. Before performed a surgery, in general, a doctor inserts a throat mask respiratory siphon into the mouth of the patient, thereby, the patient can breath easily. The position of the respiratory siphon A matching to the mouth is adhered to the face of the patient by tape P. As a result, the respiratory siphon can be fixed to the mouth of the patient so as to prevent from the movement of the respiratory siphon (since this will hurt the mucous membrane of the patient).

In surgery, although anodyne is applied to the patient, the patient possibly has convulsions, thereby, the user's teeth will bit together. Since the throat mask respiratory siphon A is a soft tube, it will deform so as to hinder the breath of the patient.

Moreover, the throat mask respiratory siphon A is fixed by tape. The operation is tedious, and the patient will feel uneasy. This fixing way is only used to fix the throat mask, while the respiratory siphon can not be guided properly.

SUMMARY OF THE INVENTION

A positioning and bit-proof throat mask retainer is a flexibly and slightly hard tube capable of being adhered to an upper side of a throat mask respiratory siphon. A lower side of the retainer is matched with an arc shape of the respiratory siphon and has a hollow cambered structure and an upper side of the retainer is suitable for the upper side of an oral cavity. A front end of the retainer is bent upwards to form as a resisting portion for resisting against an upper jaw of the patient along the cambered shape of the upper jaw. By the supporting of the upper jaw, the retainer is fixed to the mouth of a patient, thereby, having a function of guiding and positioning the respiratory siphon. When the patient contracts in surgery, the retainer is exactly positioned in the mouth of the patient. When the teeth of patient bit together, since the retainer is hard and flexible, it can resist against the upper and lower teeth of the patient. Thereby, the patient will not be hurt.

The various objects and advantages of the present invention will be more readily understood from the following detailed description when read in conjunction with the appended drawing.

BRIEF DESCRIPTION OF THE DRAWINGS

FIG. 4A is a partial enlarged view of the present invention.

DETAILED DESCRIPTION OF THE PREFERRED EMBODIMENTS

One embodiment about the present invention will be described herein with the appended drawings. Those skilled in the art may understand the functions and objects of the present invention from the following description.

Figure 1:
FIG. 1 shows one embodiment of the prior art.
Figure 2:
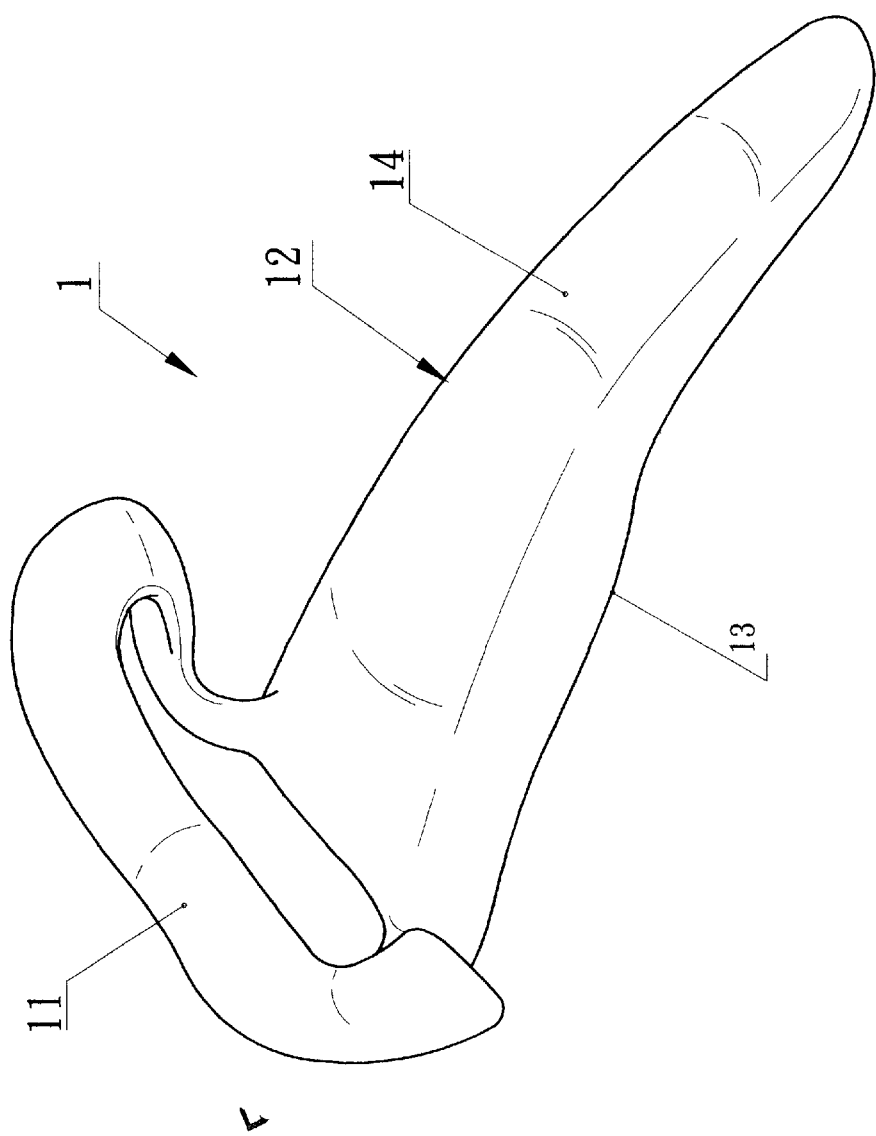
FIG. 2 is a perspective view of the present invention.
Figure 3:
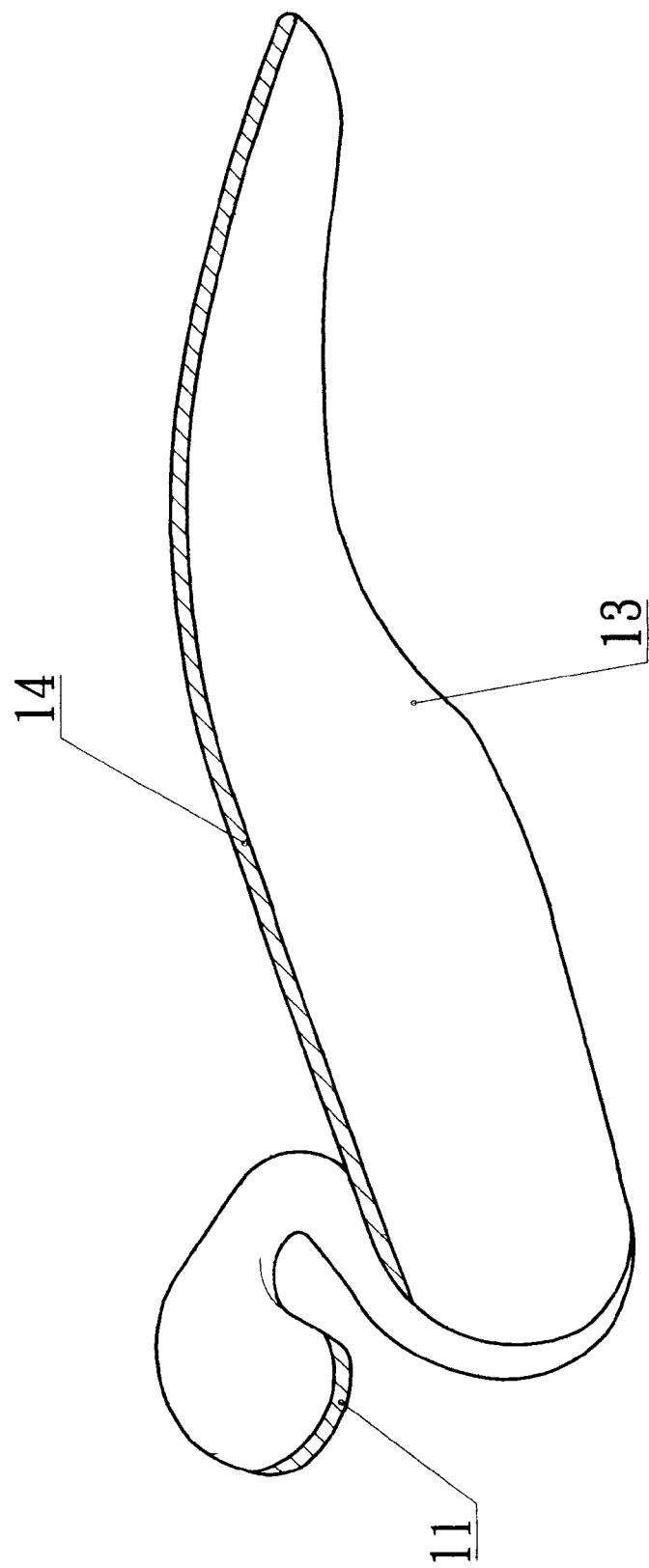
FIG. 3 is a plane cross section view of the present invention.
Figure 4:
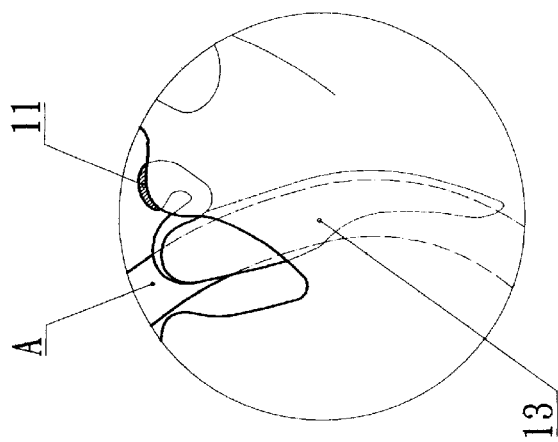
FIG. 4 shows one embodiment of the present invention.
Figure 4:
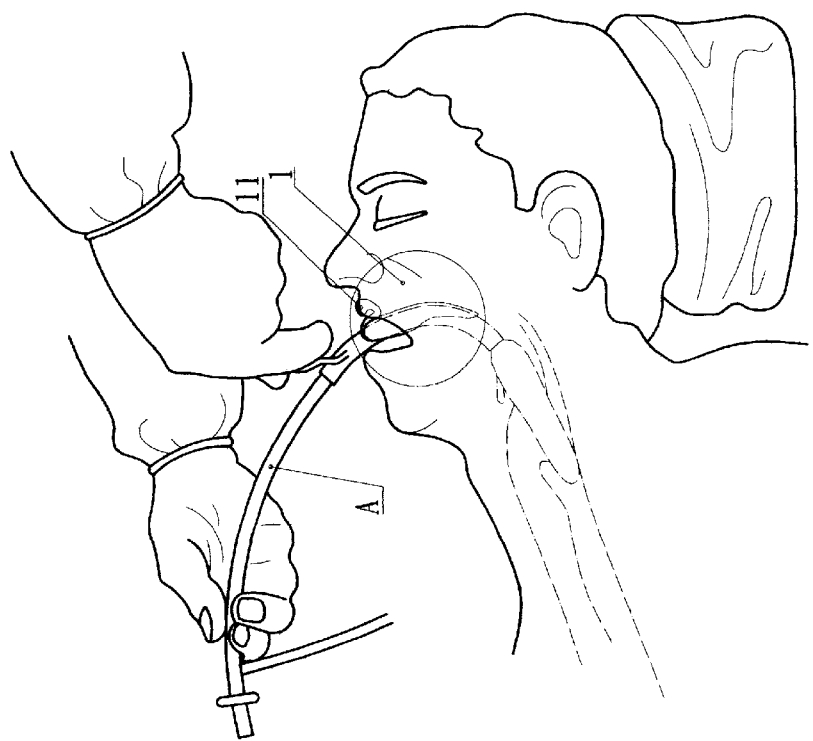

Referring to FIGS. 1 and 2, the structure of the present invention is clearly illustrated. The retainer 1 of the present invention is a flexibly and slightly hard tube which is adhered to an upper side of a respiratory siphon A of a throat mask of a patient. A lower side of the retainer is matched with the arc of the respiratory siphon A and has a hollow cambered tube structure. The upper side of the retainer is suitable for the shape of oral cavity. A front end of the retainer is bent forwards to be formed as a resisting portion 11. The resisting portion 11 resists against the upper jaw of the patient along the cambered shape of the upper jaw. By the supporting of the upper jaw, the retainer 1 is fixed to the mouth of the patient, thereby, having the function of guiding and positioning the respiratory siphon.

The operation of the present invention will be described herein. When the patient contracts in surgery, the retainer 1 is exactly positioned in the mouth of the patient. When the teeth of patient bit together, since the retainer 1 is hard and flexible, it can resist against the upper and lower teeth of the patient. Thereby, the patient will not hurt himself (or herself). As a result, a positioning and bit-proof throat mask retainer is formed.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A positioning and bit-proof throat mask retainer; said throat mask retainer being a flexibly and slightly hard tube capable of being adhered to an upper side of a throat mask respiratory siphon; the throat mask comprising:

a rear end comprising a lower side and an upper side;

the lower side has a hollow cambered structure for matching an arc shape of the respiratory siphon;

the upper side having a cambered shape conformed with the shape of an upper side of human oral cavity; an inner side of the lower side being lowered so as to receiving a respiratory siphon; and a front end of the retainer being bent upwards to form a resisting portion for resisting against an upper jaw of a patient;

wherein a lateral side of the front end having an S shape, that is, the front end extending upwards from the rear end, then bending backwards toward the rear end and then further bending forwards; thereby, having a function of guiding and positioning the respiratory siphon;

wherein when the patient contracts in surgery, the retainer is exactly positioned in the mouth of the patient; when teeth of the patient bit; since the retainer is hard and flexible, it resists against upper and lower teeth of the patient; thereby, the patient will not be hurt.

* * * * *